US009737430B2

(12) United States Patent
Gaylord

(10) Patent No.: US 9,737,430 B2
(45) Date of Patent: *Aug. 22, 2017

(54) ANKLE STABILIZING APPARATUS HAVING A DYNAMIC CUFF AND STABILIZING STRAP SYSTEM

(71) Applicant: MEDICAL SPECIALITIES, INC., Charlotte, NC (US)

(72) Inventor: Eric Lee Gaylord, Matthews, NC (US)

(73) Assignee: MEDICAL SPECIALTIES, INC., Charlotte, NC (US)

(*) Notice: Subject to any disclaimer, the term of this patent is extended or adjusted under 35 U.S.C. 154(b) by 604 days.

This patent is subject to a terminal disclaimer.

(21) Appl. No.: 14/275,092

(22) Filed: May 12, 2014

(65) Prior Publication Data

US 2014/0249460 A1    Sep. 4, 2014

Related U.S. Application Data

(63) Continuation of application No. 12/062,621, filed on Apr. 4, 2008, now Pat. No. 8,721,578.

(60) Provisional application No. 60/982,543, filed on Oct. 25, 2007.

(51) Int. Cl.
*A61F 13/00* (2006.01)
*A61F 5/01* (2006.01)

(52) U.S. Cl.
CPC .......... *A61F 5/0102* (2013.01); *A61F 5/0111* (2013.01)

(58) Field of Classification Search
CPC ...... A61F 5/011; A61F 5/0193; A61F 5/0113; A61F 13/066; A61F 5/0116; A61F 5/0217; A61F 5/0127

USPC ............................ 602/23, 27; D24/190–192
See application file for complete search history.

(56) References Cited

U.S. PATENT DOCUMENTS

| 540,931 A | 6/1895 | Walkey |
| 921,563 A | 5/1909 | Weber et al. |
| 3,308,829 A | 3/1967 | Edwards |
| 3,926,186 A | 12/1975 | Nirschl |
| 4,433,682 A | 2/1984 | Badra |
| 4,651,726 A | 3/1987 | Holland |
| 4,926,846 A | 5/1990 | Nassar |

(Continued)

FOREIGN PATENT DOCUMENTS

| AU | 2008317265 | 1/2014 |
| EP | 2203135 | 4/2009 |
| WO | 2009/055080 A1 | 4/2009 |

OTHER PUBLICATIONS

Redacted Transcript of Deposition of Eric Lee Gaylord taken on Sep. 1, 2011; 237 pages.

(Continued)

*Primary Examiner* — Kim M Lewis
(74) *Attorney, Agent, or Firm* — Additon, Higgins & Pendleton, P.A.

(57) ABSTRACT

An ankle stabilizing apparatus for minimizing inversion and eversion of the foot includes a body member having at least one cuff member positioned against a cuff portion of the body member, wherein the cuff member defines at least one opening for receiving at least one stabilizing strap such that the cuff member and stabilizing strap dynamically apply a variable force against the body member and ankle. The apparatus promotes variable compression against the ankle upon application and during wear. The apparatus also resists distal migration during wear.

36 Claims, 4 Drawing Sheets

(56) References Cited

U.S. PATENT DOCUMENTS

| | | | |
|---|---|---|---|
| 5,067,486 | A | 11/1991 | Hely |
| 5,069,202 | A | 12/1991 | Prock |
| 5,090,404 | A | 2/1992 | Kallassy |
| 5,209,722 | A | 5/1993 | Miklaus et al. |
| 5,242,379 | A | 9/1993 | Harris et al. |
| 5,511,323 | A | 4/1996 | Dahlgren |
| 5,778,563 | A | 7/1998 | Ahlbaumer |
| 5,795,316 | A | 8/1998 | Gaylord |
| 6,021,780 | A | 2/2000 | Darby |
| 6,053,884 | A | 4/2000 | Peters |
| 6,379,321 | B2 | 4/2002 | Gaylord et al. |
| 6,394,971 | B1 | 5/2002 | Slautterback et al. |
| 6,540,705 | B2 | 4/2003 | Norstrem et al. |
| 6,629,945 | B1 | 10/2003 | Stromgren |
| 6,652,474 | B1 | 11/2003 | Quinn et al. |
| 6,663,583 | B1 | 12/2003 | Janis |
| 7,252,647 | B1 * | 8/2007 | Hely ............... A61F 5/0111 128/882 |
| 7,651,472 | B2 | 1/2010 | Gaylord et al. |
| 7,753,865 | B1 | 7/2010 | Hely |
| 7,828,758 | B2 | 11/2010 | Clements et al. |
| D639,965 | S | 6/2011 | Wehsely-Swiczinsky |
| 7,993,295 | B2 | 8/2011 | Nelson |
| D649,650 | S | 11/2011 | Wehsely-Swiczinsky |
| D649,651 | S | 11/2011 | Weaver, II et al. |
| 8,721,578 | B2 * | 5/2014 | Gaylord ............ A61F 5/0111 602/23 |
| 8,808,215 | B2 | 8/2014 | Gaylord |
| 9,375,339 | B2 | 6/2016 | Gaylord |
| 9,393,146 | B2 | 7/2016 | Gaylord |
| 2002/0077576 | A1 | 6/2002 | Saraceni |
| 2003/0083603 | A1 | 5/2003 | Nelson |
| 2003/0100855 | A1 | 5/2003 | Norstrem |
| 2004/0078999 | A1 | 4/2004 | Freed |
| 2004/0215123 | A1 | 10/2004 | Slautterback et al. |
| 2006/0004311 | A1 | 1/2006 | Hargrave et al. |
| 2006/0211968 | A1 | 9/2006 | Gordon et al. |
| 2007/0213649 | A1 | 9/2007 | Gaylord et al. |
| 2009/0112140 | A1 | 4/2009 | Gaylord et al. |
| 2013/0012855 | A1 | 1/2013 | Giza et al. |
| 2014/0249460 | A1 | 9/2014 | Gaylord |

OTHER PUBLICATIONS

Exhibit 1 from Deposition of Eric Lee Gaylord taken on Sep. 1, 2011; Declaration of Eric Lee Gaylord Under Rule 56 filed in the U.S. Patent Office on Jul. 13, 2011; 4 pages.

Exhibit 2 from Deposition of Eric Lee Gaylord taken on Sep. 1, 2011; Defendant's Initial Disclosures Under Rule 26(a)(1) filed in U.S. District Court, Western Division of NC on Feb. 28, 2011; 6 pages.

Exhibit 3 from Deposition of Eric Lee Gaylord taken on Sep. 1, 2011; U.S. Pat. No. 5,067,486 Issued Nov. 26, 1991; 9 pages.

Exhibit 4 from Deposition of Eric Lee Gaylord taken on Sep. 1, 2011; Presentation of New ASO Brace Ideas by C. Steven Yates dated Apr. 17, 1996; 40 pages.

Exhibit 5 from Deposition of Eric Lee Gaylord taken on Sep. 1, 2011; Presentation of New ASO Brace Ideas by C. Steven Yates dated Apr. 17, 1996; 39 pages.

Exhibit 6 from Deposition of Eric Lee Gaylord taken on Sep. 1, 2011; Letter to Mr. Yates from Ed Durkin dated Apr. 19, 1996; 1 page.

Exhibit 7 from Deposition of Eric Lee Gaylord taken on Sep. 1, 2011; Memo to Mr. Yates from Mr. Eric Gaylord dated Aug. 1, 1996; 1 page.

Exhibit 8 from Deposition of Eric Lee Gaylord taken on Sep. 1, 2011; U.S. Pat. No. 5,795,316 issued Aug. 18, 1998; 17 pages.

Exhibit 9 from Deposition of Eric Lee Gaylord taken on Sep. 1, 2011; Images of Prototypes; 19 pages.

Exhibit 10 from Deposition of Eric Lee Gaylord taken on Sep. 1, 2011; Documents Related to ASO EVO Application; 55 pages.

Exhibit 11 from Deposition of Eric Lee Gaylord taken on Sep. 1, 2011; Amendment and Response filed in U.S. Patent Office on Jan. 27, 2011; 22 pages.

Exhibit 12 from Deposition of Eric Lee Gaylord taken on Sep. 1, 2011; Email dated Jul. 29, 2008; 1 page.

Exhibit 42 from Deposition of Ed Durkin taken on Oct. 31, 2011; Memo to Mr. Yates from Eric Gaylord dated Aug. 1, 1996; 1 page.

Exhibit 45 from Deposition of Ed Durkin taken on Oct. 31, 2011; Memo regarding modification version dated May 19, 1997; 1 page.

Exhibit 46 from Deposition of Ed Durkin taken on Oct. 31, 2011; Memo regarding Syndesmosis Brace dated Nov. 1, 1996; 1 page.

Exhibit 55 from Deposition of Ed Durkin taken on Oct. 31, 2011; Memo regarding Mr. Yates' ASO Ideas dated Apr. 19, 1996; 1 page.

Exhibit 57 from Deposition of Ed Durkin taken on Oct. 31, 2011; Letter to Mr. Yates from Ed Durkin dated Apr. 19, 1996; 4 pages.

Plaintiff's Responses to Defendant's First Set of Interrogatories served on Sep. 6, 2011; 21 pages.

Plaintiff's Responses to Defendant's First Set of Requests for Production of Documents and Things; 16 pages.

Condensed Portions from Deposition of Edward T. Durkin taken on Oct. 31, 2011 relating to 45, 46, 54, 55 and 57, including Exhibit Index; 10 pages.

Exhibit 42 from Deposition of Edward T. Durkin taken on Oct. 31, 2011; Memo to Mr. Yates from Mr. Eric Gaylord dated Aug. 1, 1996; 1 page.

Exhibit 45 from Deposition of Edward T. Durkin taken on Oct. 31, 2011; Memo regarding modification version dated May 19, 1997; 1 page.

Exhibit 46 from Deposition of Edward T. Durkin taken on Oct. 31, 2011; Memo regarding Syndesmosis Brace dated Nov. 1, 1996; 1 page.

Exhibit 54 from Deposition of Edward T. Durkin taken on Oct. 31, 2011; Presentation of New ASO Brace Ideas by C. Steven Yates dated Apr. 17, 1996; 42 pages.

Exhibit 55 from Deposition of Edward T. Durkin taken on Oct. 31, 2011; Memo regarding Mr. Yates' ASO Ideas dated Apr. 19, 1996; 1 page.

Exhibit 57 from Deposition of Edward T. Durkin taken on Oct. 31, 2011; Letter to Mr. Yates from Ed Durkin dated Apr. 19, 1996; 2 pages.

Redacted Portions of Transcript of Deposition of C. Steven Yates taken on Aug. 3, 2012; 89 pages.

Exhibit 2 from Deposition of C. Steven Yates taken on Aug. 3, 2012; Presentation of New Brace Ideas by C. Steven Yates; 40 pages.

Exhibit 3 from Deposition of C. Steven Yates taken on Aug. 3, 2012; U.S. Pat. No. 4,878,504 issued Nov. 7, 1989; 13 pages.

Exhibit 4 from Deposition of C. Steven Yates taken on Aug. 3, 2012; U.S. Pat. No. 4,313,433 issued Feb. 2, 1982; 12 pages.

Redacted Portions of Transcript of Deposition of C. Steven Yates taken on Aug. 24, 2012; 99 pages.

Exhibit 29 from Deposition Transcript of C. Steven Yates taken on Aug. 24, 2012; Log of C. Steven Yates from 1996-2009 consisting of personal face to face contacts, meetings, seminars, lectures, classes, conventions, telephone conversations, faxes, mailings, and testimonials pertaining to the promotion, marketing, and sales of the ASO and like products produced and sold by Medical Specialties, Inc.; 35 pages.

Exhibit 30 from Deposition Transcript of C. Steven Yates taken on Aug. 24, 2012; Agreement regarding New ASO Brace Ideas Apr. 29, 1996; 1 page.

Exhibit 34 from Deposition Transcript of C. Steven Yates taken on Aug. 24, 2012; Susan Yates to Scott Gaylord and Eric Gaylord Jul. 29, 2008; 1 page.

Exhibit 35 from Deposition Transcript of C. Steven Yates taken on Aug. 24, 2012; U.S. Patent Application Publication No. 20090112140; 15 pages.

Exhibit 36 from Deposition Transcript of C. Steven Yates taken on Aug. 24, 2012; Pages from New Brace Ideas; 8 pages.

Plaintiff's Supplemental Brief Regarding Similarities Between the '486 Patent and ASO Devices Other Than the ASO Axis; Filed Aug. 20, 2012; 12 pages.

(56) References Cited

OTHER PUBLICATIONS

Exhibit 38 from Deposition Transcript of C. Steven Yates taken on Aug. 24, 2012; Declaration of C. Steven Yates Aug. 20, 2012 with exhibits A through M; 149 pages.
Medical Specialties Inc.'s Response to the Court's Request for Proposed Order and Supplemental Briefing; Filed Aug. 31, 2012; 26 pages.
Exhibit 44 from Deposition Transcript of C. Steven Yates taken on Aug. 24, 2012; U.S. Pat. No. 3,073,305 issued Jan. 15, 1963; 7 pages.
Exhibit 45 from Deposition Transcript of C. Steven Yates taken on Aug. 24, 2012; Handwritten notes of Mr. Yates of Oct. 15, 1994, 1 page.
Exhibit 52 from Deposition Transcript of C. Steven Yates taken on Aug. 24, 2012; Letter from Steve Yates to Rick Gaylord dated Jul. 12, 2000; 4 pages.
Plaintiff's Supplemental Responses to Defendant's First Set of Interrogatories; Filed Oct. 10, 2012; 11 pages.
Complaint filed by C. Steven Yates against Medical Specialties on Dec. 6, 2010 in the State of North Carolina, Civil Case 3:11-cv-0006; 16 pages.
Defendant's Answer and Counterclaims to Complaint filed Jan. 12, 2011 in Civil Case 3:11-cv-0006; 20 pages.
Reply to Counterclaim filed Feb. 2, 2011 in Civil Case 3:11-cv-0006; 13 pages.
Presentation of New ASO Brace Ideas by C. Steven Yates dated Apr. 17, 1996; 39 pages.
Photographs of Prototype 1; 11 pages.
Photographs of Prototype 2, 8 pages.
PCT International Search Report in counterpart International Application No. PCT/US2008/052449 mailed Jul. 30, 2008, 2 pages.
International Preliminary Report on Patentability in counterpart International Application No. PCT/US2008/052449 dated Apr. 27, 2010, pp. 1-9.
Extended European Search Report and Written Opinion in counterpart European Application No. 08714126.3 dated Nov. 17, 2014, pp. 1-6.
Office Action in counterpart Australian Application No. 2008317265 dated Jan. 4, 2013, pp. 1-3.
Certificate of Grant in counterpart Australian Application No. 2008317265 dated Jan. 30, 2014, p. 1.
Office Action in counterpart Canadian Application No. 2,703,266 dated Nov. 6, 2014, pp. 1-4.
Office Action in counterpart Canadian Application No. 2,703,266 dated Jan. 23, 2014, pp. 1-3.
Provisional Application for "Ankle Stabilizing Apparatus Having a Dynamic Cuff and Stabilizing Strap System" U.S. Appl. No. 60/982,543, filed Oct. 25, 2007, pp. 1-20.
Intention to Grant with text intended for grant in counterpart European Application No. 08714126.3 dated Apr. 18, 2017, pp. 1-94.

\* cited by examiner

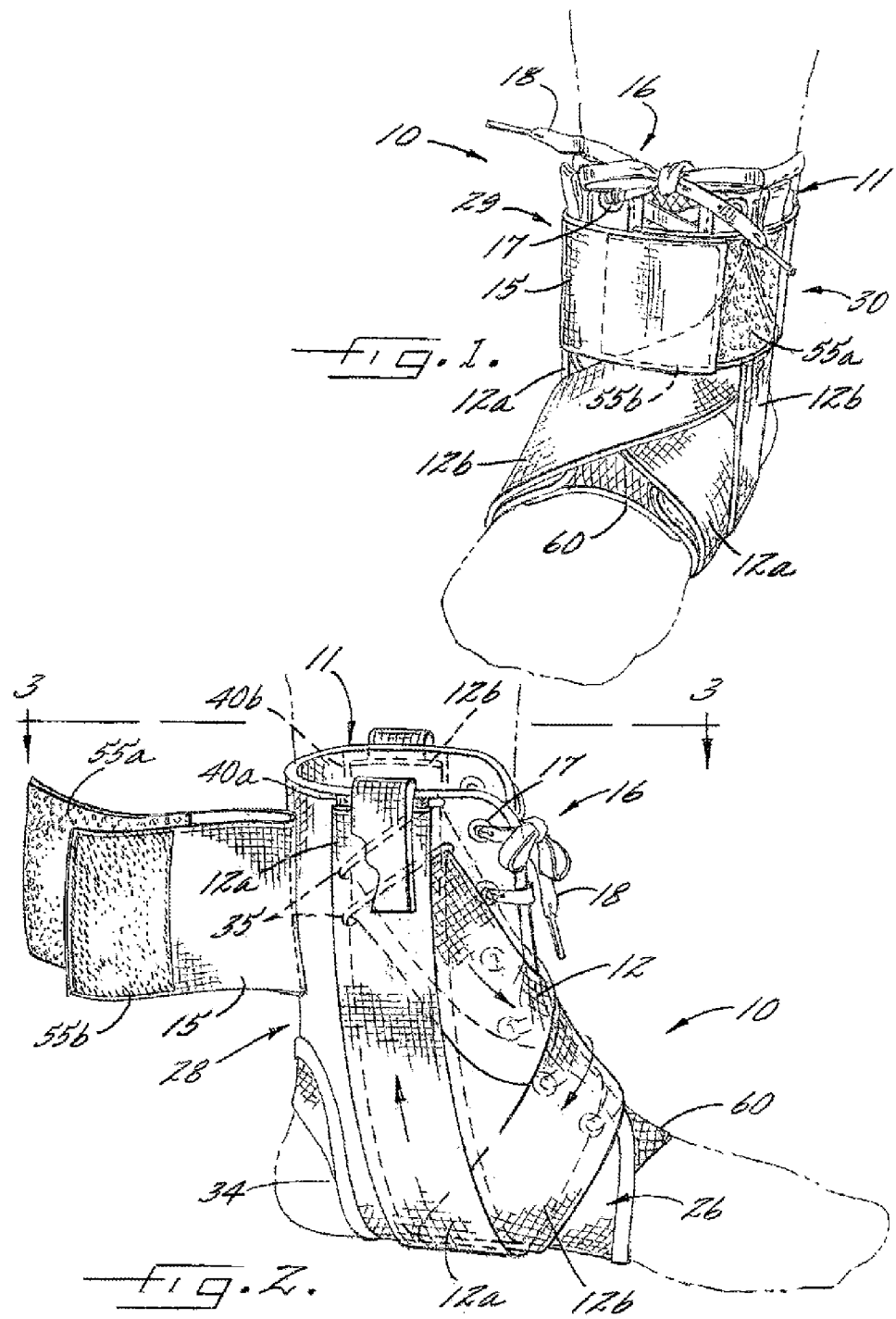

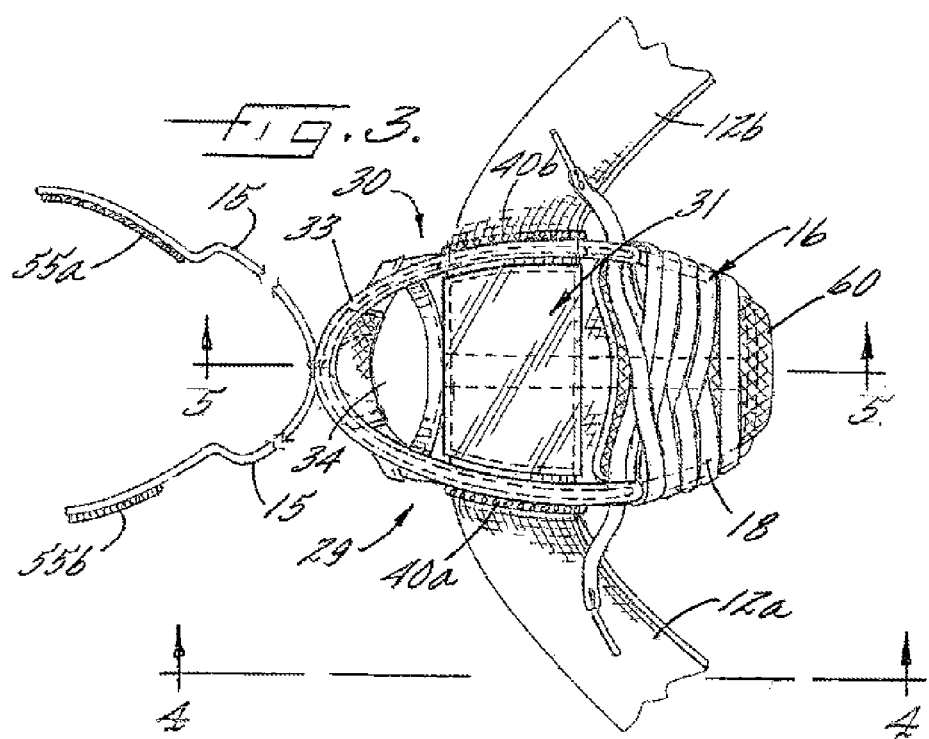
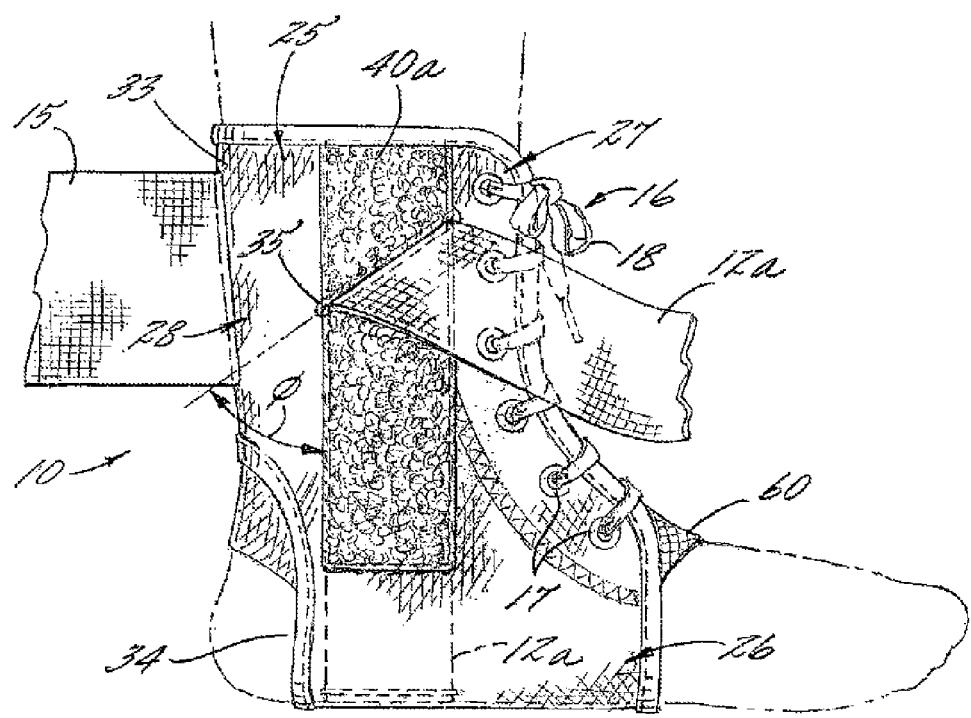

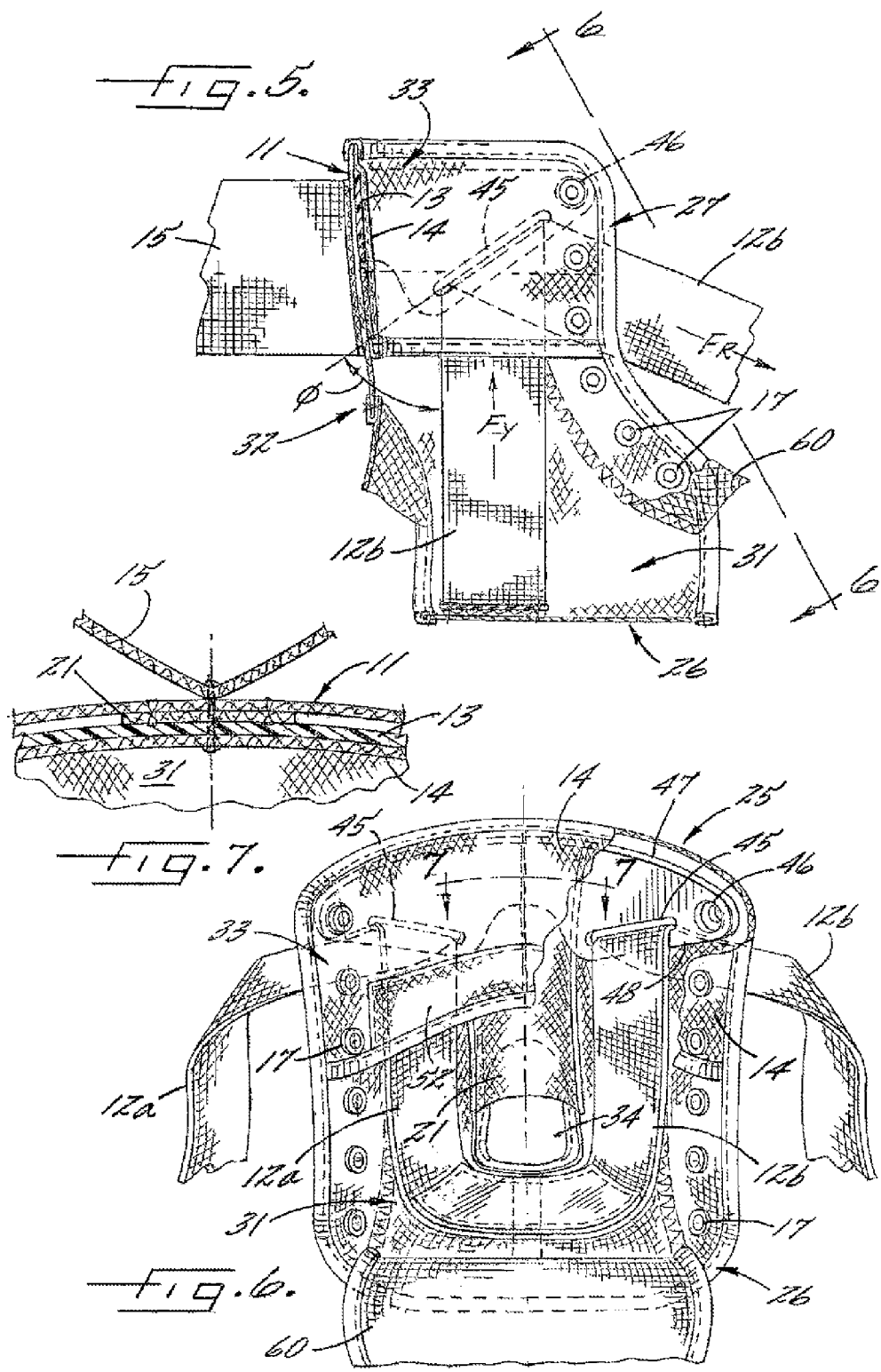

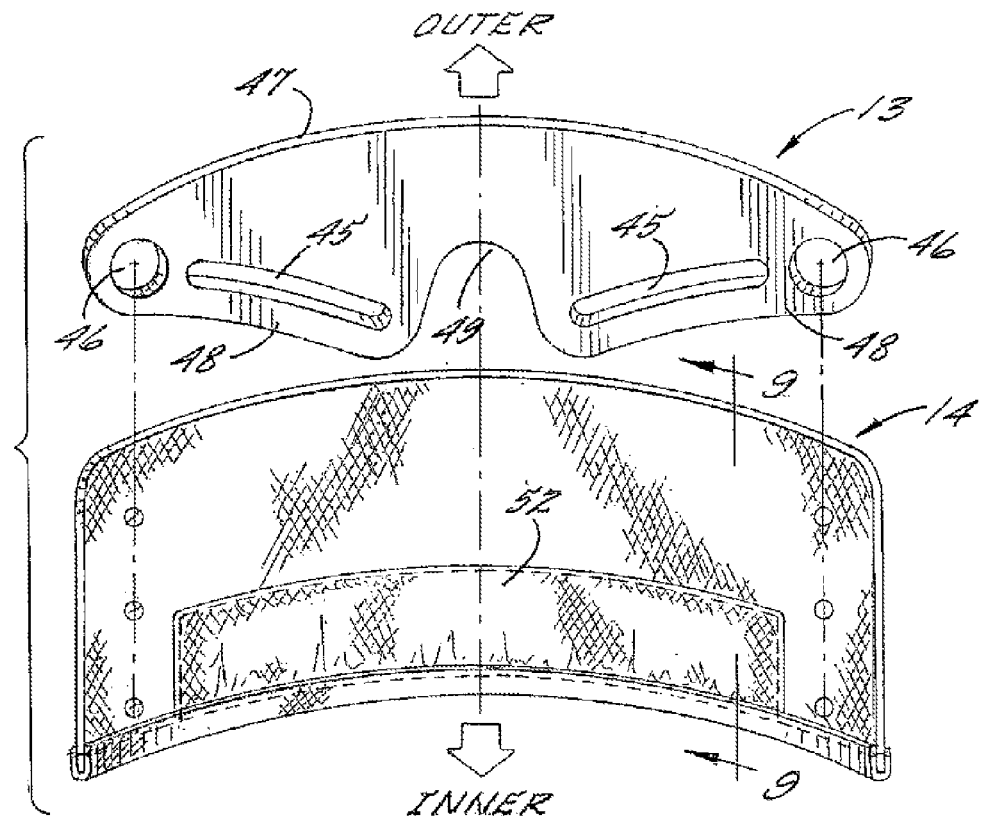
Fig. 8.
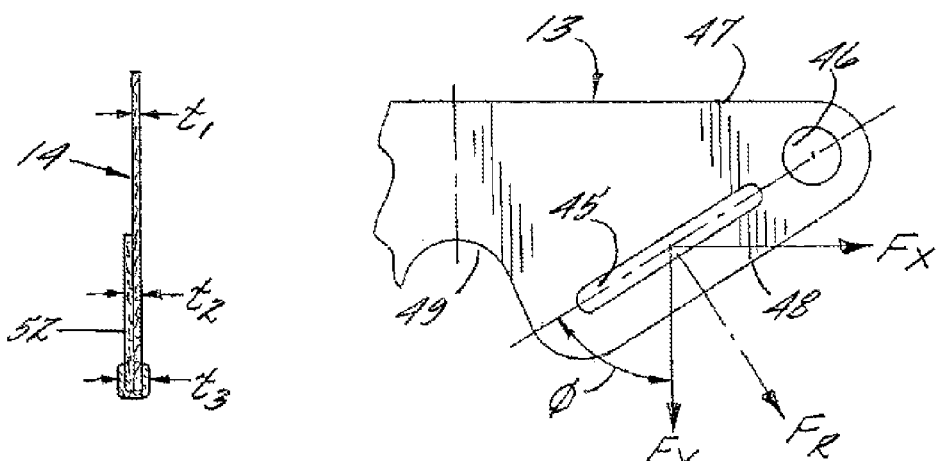
Fig. 9.
Fig. 10.

ANKLE STABILIZING APPARATUS HAVING A DYNAMIC CUFF AND STABILIZING STRAP SYSTEM

CROSS-REFERENCE TO PRIORITY APPLICATIONS

This application is a continuation of commonly assigned U.S. patent application Ser. No. 12/062,621, filed Apr. 4, 2008, now U.S. Pat. No. 8,721,578, and claims the benefit of commonly assigned PCT Application No. PCT/US08/52449, filed Jan. 30, 2008, in the U.S. Patent and Trademark Office, which designates the U.S., and claims priority to commonly assigned U.S. Provisional Patent Application Ser. No. 60/982,543, filed Oct. 25, 2007, in the U.S. Patent and Trademark Office. This application incorporates the non-provisional, PCT, provisional, and provisional applications by reference in their entirety.

BACKGROUND OF THE INVENTION

The invention relates to an ankle stabilizing apparatus for minimizing inversion and eversion of the foot, and more specifically, to a body member having at least one cuff member affixed to a cuff portion of the body member, wherein the cuff member defines at least one opening for receiving at least one stabilizing strap. As configured, the cuff and stabilizing strap dynamically apply a varying force against the body member and ankle during application and use. In other words, the cuff and stabilizing strap system applies a variable amount of tension and compression to thereby restrict movement of the body member relative to an ankle of an individual.

As known to participants in athletics, the ankle is often injured as a result of contact with other participants or equipment, or as a result of the ankle assuming an unnatural position during play. Injuries typically occur during motions associated with athletics such as running, jumping, falling, or the like. Specifically, ankles are particularly vulnerable to sprains, fractures, and the like.

Athletes at risk for ankle injuries often utilize some form of ankle support during participation in sporting events. A large number of ankle injuries occur when the foot rolls inwardly (referred to as "eversion") or outwardly (referred to as "inversion") from the leg. Many athletes rely upon taping to provide supplemental ankle support, whereby the athlete or trainer winds athletic tape around the athlete's ankle to thereby limit the motion of the ankle relative to the leg. Although taping stabilizes the ankle against undesired motion, a number of drawbacks exist. For example, taping may restrict all motion of the ankle, both desirable and undesirable, because the tape is wound circumferentially around the ankle. The restrictive characteristics of taping thus hinder the athlete's ability to perform. Further, tape tends to stretch and loosen as the athlete moves, thereby decreasing its effectiveness in supporting the ankle.

The majority of ankle sprains are caused by eversion and inversion of the foot. Seventy-five to ninety percent (75-90%) of sprains are attributable to inversion (i.e., outward rolling of the foot). Moreover, undesirable movement of the ankle may occur as a result of lateral or vertical movement of upper portions of the body member relative to lower portions of the body member.

SUMMARY OF THE INVENTION

The ankle stabilizing apparatus comprises in one embodiment a flexible body member for receiving portions of a foot and ankle, at least one stabilizing strap positioned against portions of the body member for securing the body member to the ankle and foot in an overlying fashion, and a shaped rigid or semi-rigid cuff member affixed to a cuff portion of the body member. A cuff enclosure is provided to position the cuff member against the body member. The apparatus may also include at least one pair of corresponding fasteners for securing a free end of the stabilizing strap to an exterior surface of the body member, at least one binding strap secured to a portion of the body member, at least one pair of corresponding fasteners for securing the free ends of the binding strap about the body member, and a body member connector for securing front edges of the body member to one another.

In more detail, an upper rear portion of the apparatus forms a closure near the distal end of the lower leg, yet above both the medial and lateral malleolli of the ankle. In one novel aspect, the cuff member is affixed to the upper and rear portions (i.e., cuff) of the apparatus. The cuff member may be formed of a semi-rigid plastic having one or more openings for receiving portions of the stabilizing strap. In one embodiment, the cuff member includes two angled, spaced-apart openings or elongate slots for receiving free ends of the stabilizing strap. As configured, the cuff member and stabilizing strap apply variable forces (i.e., tension and compression) against the body member and an individual's ankle and lower leg during use.

In one embodiment, one end of the stabilizing strap is positioned against an interior surface of a lower portion of the body member. Advantageously, the cuff member serves as an anchor for the pulley-like effect as the stabilizing strap passes through the slots in the cuff member. As the foot and ankle rotate (i.e., eversion or inversion) during use, a portion of the stabilizing strap positioned against an exterior surface of the body member is drawn tighter. The tightening of this portion of the stabilizing strap transmits an increased amount of tension to the portion of the stabilizing strap positioned against the interior surface of the body member (i.e., the stirrup portion of the strap that passes under the heel). The increased tension on the stabilizing strap applies compression against the body member and ankle to thereby stabilize the ankle and foot, and prevent a sprain. Thus, the apparatus dynamically responds to the movement of the ankle and body member during use and provides increased stability.

The stabilizing strap may include grip-enhancing fabric in the heel area adjacent to the foot to thereby transfer the tensioning force against the foot. Tensioning of the stabilizing strap during application and use promotes grip and secures the heel to reduce the amount of foot and ankle rotation, and thereby reduce tendon strain (e.g., an ankle sprain).

In one embodiment illustrated in FIG. 10, the angled slots in the cuff member create X and Y axis components of force when the strap is tensioned (i.e., $F_X$ and $F_Y$, respectively). The combination of the X and Y force components results in a resultant force (i.e., $F_R$). The $F_X$ force component acting on the stabilizing strap varies the tension in the cuff of the apparatus. Tension in the cuff is caused by tension applied by portions of the stabilizing strap positioned against exterior surfaces of the body member. Specifically, the $F_X$ force component results in cylindrical tightening of the cuff (i.e., compression) which aids in the reduction of the high-ankle sprain injury known as syndesmosis. The cuff of the apparatus is dynamic in the sense that the cuff member promotes increased compression when the stabilizing strap is tightened both during application and when the apparatus actively restricts ankle rotation (i.e., during use). As configured, the dynamic tightening of the cuff minimizes the effects of syndesmosis by applying increased compression the moment the foot is under load and rotates excessively.

The $F_Y$ force component acting on the stabilizing strap varies the tension in an interior stirrup region of the body member. Thus, the user may adjust tension applied by portions of the stabilizing strap positioned against an interior surface of the body member after securely lacing the boot. This configuration simultaneously allows the tensioning of the strap portions positioned against interior surfaces of the body member (i.e., stirrup region) and the strap portions positioned against exterior surfaces of the body member (i.e., portions as applied in an overlying FIG. 8 pattern about the body member). Advantageously, the resultant force ($F_R$) or $F_R$ force component provides the simultaneous tensioning of the strap portions positioned against the interior and exterior surfaces of the body member.

Distal migration can be a problem for any flexible ankle apparatus resulting in loosening of the stabilizing strap during and after application. Any upward force exerted by the strap on the foot and ankle in the process of counteracting rotation is met with an equal and opposite downward force on the upper region of the apparatus where the strap is adjustably secured to the body member. The downward force contributes to distal migration of the body member.

The dynamic cuff and stabilizing strap system of the present ankle apparatus comfortably and effectively addresses the issue of distal migration through the aforementioned variable compression (which increases with increased foot rotation) and by introducing an inverted, truncated cone shape which mirrors the anatomy of the typical lower leg. The inverted, truncated cone shape of the cuff of the body member is accomplished by introducing variable thickness in the vertical direction to the cuff enclosure. This is accomplished by incorporating a strip of material (e.g., fabric) or a flexible sheet member on the interior surface of the cuff enclosure as applied against the cuff member and interior surface of the body member. The flexible sheet member may partially cover the inferior or lower portion of the cuff enclosure. The application of the flexible sheet member to the cuff enclosure results in an increased circumference of the lower cuff which is substantially adjacent to the leg at its minimum thickness just above the malleolli of the ankle. In one embodiment, the thickness of the cuff is approximately 33% greater near the lower edge of the cuff member where the lower leg and ankle are narrower. This configuration permits an outermost binding strap—which may cover the cuff as the final step in application—to compress the cuff across a greater area in a more uniform fashion because the exterior surface of the cuff defines a more geometrically accurate cylindrical shape.

In another novel aspect, the stabilizing strap is positioned against the ankle apparatus under the calcaneous region and symmetrically advances upward against the interior surface of the opposing sides of the body member to the cuff member. In one embodiment, the stabilizing strap extends upwardly, passes through the openings in the cuff member, and advances outwardly exterior of the body member. The stabilizing strap then encircles the foot by crossing over the dorsum of the foot (i.e., anterior or upper surface), under the heel, and upwardly against an exterior side portion of the body member in a FIG. 8 formation where it is removably attached with a fastener to an exterior surface of the body member. As configured, the stabilizing strap beneficially forms both an inner heel stirrup and an outer FIG. 8 formation with one adjustable strap.

BRIEF DESCRIPTION OF THE DRAWINGS

The foregoing and other objects and advantages of the invention and the manner in which the same are accomplished will become clearer based on the following detailed description taken in conjunction with the accompanying drawings in which:

FIG. 1 is a perspective view of one embodiment of the ankle stabilizing apparatus of the invention;

FIG. 2 is a perspective view of one embodiment of the ankle stabilizing apparatus of FIG. 1;

FIG. 3 is a partial top plan view of one embodiment of the ankle stabilizing apparatus of FIG. 1;

FIG. 4 is a side view of the ankle stabilizing apparatus of FIG. 1 taken generally along line 4-4 of FIG. 3;

FIG. 5 is a partial cross-sectional view of the ankle stabilizing apparatus of FIG. 1 taken generally along line 5-5 of FIG. 3;

FIG. 6 is a partial front perspective view of the ankle stabilizing apparatus of FIG. 1 taken generally along line 6-6 of FIG. 5;

FIG. 7 is an enlarged sectional view of the ankle stabilizing apparatus of FIG. 1 taken generally along line 7-7 of FIG. 6;

FIG. 8 is an enlarged perspective view of the cuff member and cuff enclosure of the ankle stabilizing apparatus of FIG. 1;

FIG. 9 is a cross-sectional view of a portion of the cuff enclosure of the ankle stabilizing apparatus of FIG. 1 taken generally along line 9-9 of FIG. 8; and FIG. 10 is an enlarged sectional view of a portion of the cuff member of the ankle stabilizing apparatus of FIG. 1.

DETAILED DESCRIPTION OF THE INVENTION

The present invention will now be described more fully hereinafter with reference to the accompanying drawings, in which a preferred embodiment of the invention is shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

An overall view of an embodiment of an ankle apparatus of the invention is set forth at 10 in the perspective view of FIG. 1. The apparatus 10 may be worn without an athletic sock such that interior surfaces of the apparatus contact skin of the individual. Alternatively, the apparatus 10 may be worn over an athletic sock such that interior surfaces of the apparatus contact the sock. Further, the apparatus 10 is configured for wear on the right or left foot. Therefore FIG. 1 illustrates the apparatus 10 as it appears when worn on a right foot. When worn on a left foot, the apparatus 10 would be a mirror-image version of the one illustrated in FIG. 1.

As illustrated in FIGS. 1 and 5, the apparatus 10 may include a flexible body member 11, at least one stabilizing strap 12 having strap portions 12a, 12b positioned against the body member, a cuff member 13 positioned against the body member for creating variable strap tension, and a cuff enclosure 14 for positioning the cuff member against the body member. As depicted in FIG. 2, the apparatus 10 may also include at least one binding strap 15 positioned against the body member 11, a body member connector 16 for securing free front edges of the body member 11, and a tongue 60. A "free edge" refers to an edge that does not intersect with another surface or portion of the apparatus.

Referring to the exemplary embodiment of the apparatus 10 depicted in FIGS. 2, 5, and 6, the configuration of the elements about the apparatus will be summarized as follows, with alternative embodiments discussed thereafter. Upon application of the apparatus 10 to a foot and ankle, a portion of the stabilizing strap 12 extends from an interior surface 31 of a lower portion 26 of the body member 11, upwardly along an interior surface 31 of one side of the body member 11, between the cuff enclosure 14 and cuff member 13, and through an opening 45 in the cuff member. Thereafter, as depicted in FIG. 4, the stabilizing strap 12 travels through an opening 35 in an upper portion 25 of the body member 11 and extends exterior therefrom. Referring to FIG. 2, the stabilizing strap 12 then extends across the front portion 27 of the body member 11 and anterior portion of the foot, against the lower portion 26 of the body member and under the heel area, and then upwardly along the exterior side of the body member from which the strap 12 extended therefrom. A free end of the stabilizing strap 12 is then releasably attached to the exterior surface 32 of the upper portion 25 of the side of the body member 11 from which the strap extends.

The flexible body member 11 is shaped to receive a foot and ankle, and defines an upper portion 25, a lower portion 26, a front portion 27, and a rear portion 28. Referring to FIG. 4, it will be understood that the term "portion" refers to various areas of the apparatus 10. It will be further understood that the terms "upper portion" and "lower portion" may also refer to "lower portion" and "upper portion", respectively, dependent upon the perspective of the individual viewing the apparatus 10. It will also be appreciated that the term "upper" implies the opposite of "lower." It will also be understood that the terms "front portion" and "rear portion" may also refer to "rear portion" and "front portion", respectively, dependent upon the perspective of the individual viewing the apparatus 10. It will also be appreciated that the term "front" implies the opposite of "rear."

Referring to FIG. 4, areas of the upper portion 25 and rear portion 28 form a cuff portion or cuff 33 of the body member 11. Stated differently, the cuff 33 extends about upper portions of the body member 11. In one embodiment, the cuff 33 extends substantially coextensive with the upper portion 25 and rear portion 28 of the body member 11.

As depicted in FIGS. 3 and 5, the body member 11 also includes a first side 29, a second side 30, an interior surface 31, and an exterior surface 32. With reference to the orientation of the brace in FIGS. 3 and 6, it will be understood that the terms "interior surface" and "exterior surface" may be referred to as "inside surface" and "outside surface." Stated differently, as used herein the term interior surface 31 implies the side of the apparatus 10 closest to the ankle or foot of the wearer. Thus, it will be understood that the term exterior surface 32 implies the side of the apparatus 10 opposite the interior surface 31 (i.e., the side farthest from the ankle or foot of the wearer).

The body member 11 may be fabricated from a pliable fabric material. Advantageously, the pliable fabric material will conform to an ankle, yet minimize any stretching familiar to elastic material. As used herein, it will be understood that the term "elastic" refers to material that is capable of being easily stretched or expanded, and resuming its former shape. Stated differently, the term elastic implies the property of resisting deformation by stretching.

One embodiment of the invention provides a body member 11 fabricated from substantially inelastic fabric material.

In a related aspect, it will be understood that the term "inelastic" refers to material that resists stretching and elongation. In this particular embodiment of the invention, the substantially inelastic material is a woven ballistic nylon fabric, as such fabrics have been found to be light weight, while providing a high degree of strength and durability. In addition, such fabrics are generally thin, a particularly desirable characteristic when an individual utilizes the apparatus inside a shoe (not shown).

The sheet of material forming the body member 11 may be formed from one or more sheets of fabric material. In one embodiment, the body member 11 is formed from one sheet of material that is capable of forming a boot-like shape. In this embodiment, the body member 11 may be referred to as a "one-piece" body member. The sheet of material is desirably folded and seamed to form a substantially L-shaped configuration for covering at least a lower and rear portion of the individual's foot and ankle. In one embodiment of the body member 11, a single sheet of fabric material is secured (e.g., stitched) at the lower portion 26 of the body member 11 (i.e., under the arch of the foot). In another embodiment, the single sheet is secured at a rear portion 28 of the body member (i.e., along the Achilles tendon area of the lower leg). In yet another embodiment, the body member 11 is formed from two sheets of fabric material (i.e., a "multipiece" body member) wherein the two sheets are secured at the lower portion 26 and rear portion 28 of the body member. In yet another embodiment, the body member 11 may be formed from a plurality of sheets secured at one or more portions of the body member.

In one embodiment, the flexible body member 11 is a boot-like body member that is substantially L-shaped and covers at least a lower and rear portion 26, 28 of the individual's foot and ankle. In this embodiment, the body member 11 includes a stirrup portion that conforms to the lower surfaces of the foot by extending under portions of the calcaneous. The body member 11 of this embodiment defines at least one opening 34 for receiving a portion of a heel.

It will be understood, however, that alternative embodiments of the apparatus 10 (not shown) may include a body member 11 without a stirrup portion. In other words, an alternative embodiment of the body member 11 has a lower edge that may end immediately below the malleoli such that the body member 11 does not extend under the foot. In this alternative embodiment, the body member 11 does not include an opening 34 for receiving a portion of a heel. Rather, the stabilizing strap 12 serves as a stirrup to secure the ankle and foot.

As illustrated in FIGS. 2 and 3, the apparatus 10 desirably includes at least one substantially inelastic stabilizing strap 12 positioned against the body member 11. For the sake of clarity, the drawings depict strap portions 12a, 12b to clearly depict the travel of the strap about the body member (see FIGS. 1 and 2). The stabilizing strap 12 secures the body member 11 to the foot and ankle in an overlying, or FIG. 8 fashion, and applies at least one force against the flexible body member during application and use. As set forth above, at least one portion of the stabilizing strap 12 is positioned against the flexible body member 11. As used herein, the phrase "positioned against" means that one element may be fixed (i.e., secured) or releasably attached to another element. Thus, the phrase "positioned against" will not exclude the option of a first element being secured or releasably attached to a second element. Accordingly, a first element may be positioned against a second element by sewing, hook and loop fasteners, or a loop that is fixed to the second element for receiving or engaging the first element. It will also be appreciated that the terms "fixed" and "secured" may include sewn, made integral with, adhered with adhesive, or bonded with heat.

Referring to FIGS. 2 and 6, one embodiment of the apparatus 10 includes one inelastic stabilizing strap 12 that has an intermediate portion (i.e., a portion between the free ends) positioned against the lower portion 26 of the body member 11, and two free ends that are removably attachable to the upper portion 25 of the body member upon application. It will be understood, however, that the apparatus 10 may include two separate inelastic stabilizing straps, wherein each strap has one end positioned against the lower portion 26 of the body member 11, and another free end that is removably attachable to the upper portion 25 of body member upon application.

In one embodiment of the invention, an intermediate portion of the stabilizing strap 12 is fixed against the interior surface 31 of the lower portion 26 of the body member 11. In another embodiment, an intermediate portion of the stabilizing strap 12 is releasably attached to the interior surface 31 of the lower portion 26 of the flexible body member 11 with, for example, corresponding hook and loop fasteners.

In yet another embodiment (not shown), an intermediate portion of the stabilizing strap 12 may be fixed against the exterior surface 32 of the lower portion 26 of the flexible body member 11. In still another embodiment (not shown), an intermediate portion of the stabilizing strap 12 may be releasably attached to the exterior surface 32 of the lower portion 26 of the flexible body member 11 with, for example, corresponding hook and loop fasteners. Accordingly, it will be understood that the intermediate portion of the stabilizing strap 12 may be fixed or releasably attached to the interior or exterior surface 31, 32 of the lower portion 26 of the flexible body member 11.

Referring to FIGS. 1 and 2, another portion of the stabilizing strap 12 is also positioned against the body member 11. In one embodiment, a free end of the stabilizing strap 12 is releasably attached to the exterior surface 32 of the upper portion 25 of the body member 11. Stated differently, the free end of the stabilizing strap 12 is removably attached to the exterior surface 32 of the first side 29 or second side 30 of the body member 11. Briefly, a free end of the stabilizing strap extends outwardly from one side of the upper portion 25 of the body member 11, over and under the foot, and back up to the side of the body member from which the strap extends. Referring to FIG. 1, a portion of the stabilizing strap 12a extending outwardly from the upper portion 25 of the first side 29 of the body member 11 is releasably attached to the exterior surface 32 of the first side 29 after being wrapped in FIG. 8 fashion over the front portion 27 of the body member 11, under the lower portion 26 of the body member, and then upwardly toward the first side 29 of the body member. Another portion of the stabilizing strap 12b extending outwardly from the second side 30 of the body member is likewise wrapped and releasably attached to the second side 30 of the body member.

In one embodiment of the invention (not shown) in which the body member 11 lacks a stirrup portion, the stabilizing strap 12 is the only element of the apparatus 10 that extends under the heel of the foot. In this embodiment, the stabilizing strap 12 is not fixed or releasably attached to the lower portion 26 of the body member 11.

In one embodiment depicted in FIGS. 2 and 5, portions of the stabilizing strap 12 extend along and substantially adjacent to portions of the interior and exterior surfaces 31, 32 of the flexible body member 11. The term "substantially adjacent" refers to two or more elements (e.g., portions) that have a common border or are in close proximity to one another. Nevertheless, it will be understood that adjacent may or may not imply contact, but always implies the absence of anything of the same kind in between.

In another embodiment (not shown), portions of the stabilizing strap 12 extend only along the interior surface 31 of the body member 11. In yet another embodiment (not shown), portions of the stabilizing strap 12 extend only along the exterior surface 32 of the body member.

For the purpose of securing the stabilizing strap 12 about the foot in the manner described below, there is provided a pair of corresponding fasteners 40 associated with each stabilizing strap. The pair of corresponding fasteners includes a first fastener 40a attached to the exterior surface 32 of the first or second side 29, 30 of the body member 11, and a second fastener 40b attached to one of the free ends of the stabilizing strap 12. The corresponding fastener pair 40 may be in the form of hook and loop fasteners of the type sold under the trademark VELCRO®.

Advantageously, the cuff member 13 directs the force applied by the stabilizing strap 12 against the flexible body member 11 and ankle during application and use. As discussed, the cuff member 13 serves as an anchor for the pulley-like effect of the stabilizing strap 12 as it passes through openings 45 in the cuff member. As the foot and ankle rotate during an activity (e.g., running), a portion of the stabilizing strap 12 positioned against an exterior surface 32 of the body member 11 is drawn tighter due to increased tension. The tightening of the portion of the stabilizing strap 12 exterior of the body member 11 transmits an increased amount of tension to the portion of the stabilizing strap 12 positioned against the interior surface 31 of the body member 11 in the stirrup portion of the strap passing under the heel. The increased tension on the stabilizing strap 12 applies compression against the body member 11 and ankle to thereby stabilize the ankle and foot and prevent a sprain. Thus, the apparatus 10 dynamically responds to the movement of the ankle and body member 11 during use and provides increased stability.

In one embodiment depicted in FIGS. 6 and 7, the cuff member 13 may be positioned against the interior surface 31 of the rear portion 28 of the flexible body member 11. In another embodiment (not shown), the cuff member 13 may be positioned against the exterior surface 32 of the rear portion 28 of the body member 11. It will also be understood that the cuff member 13 may be positioned against the interior or exterior surface of the upper portion 25 of the body member 11. Thus, the cuff member 13 may be positioned against the cuff 33—i.e., against the upper and rear portions 25, 28 of the body member.

As depicted in FIG. 8, the cuff member 13 defines at least one opening 45 for slidably receiving a portion of the stabilizing strap 12. In one embodiment, the cuff member 13 defines two openings 45 (i.e., a first and second opening) for receiving portions 12a, 12b of a single integral stabilizing strap 12 or two separate stabilizing straps extending upwardly from the lower portion 26 of the body member 11. Thus, the cuff member 13 directs the stabilizing strap 12 from a position interior of the flexible body member 11 to a position exterior of the flexible body member. Stated differently, the cuff member 13 redirects the direction of travel of the stabilizing strap 12.

As positioned on the body member 11, the cuff member 13 varies the amount of force acting on the body member during application and use to stabilize the foot and ankle.

Specifically, the cuff member 13 dynamically varies the amount of circumferential and vertical compression acting on the body member 11 when the stabilizing strap 12 is under tension. The stabilizing strap 12 is tensioned or tightened by the user during application and by motion of the foot and body member 11 during dorsiflexion and flexion of the foot when in use (e.g., running). Dorsiflexion refers to the forward movement of upper portions of the ankle with respect to the foot, whereas flexion refers to the rearward movement of upper portions of the ankle with respect to the foot.

With reference to FIGS. 5 and 10 and stated differently, the cuff member 13 redirects the vertical tension or $F_Y$ force component, which is applied by the stabilizing strap 12 against the body member 11 when the strap is pulled upward during application and use, and the horizontal tension force or $F_X$ force component, which is applied by the stabilizing strap 12 against the body member 11 when extended substantially laterally during application and use, to thereby form a resultant force $F_R$ applied against the body member 11 and foot and ankle. In other words, in conjunction with the stabilizing strap 12, the cuff member 13 redirects the force applied by the stabilizing strap to vary compression acting on the body member 11 and ankle.

Still referring to FIG. 10, one embodiment of the cuff member 13 includes angled elongate slots 45 that create the $F_X$, $F_Y$, and $F_R$ force components when the strap 12 is tensioned. In this embodiment, the angle $\Phi$ between the longitudinal axis of the elongate slot and vertical axis Y of the body member 11 is approximately 45°. That said, it will be understood that the angle may be any number of degrees so long as the cuff member 13 is capable of directing forces applied by the stabilizing strap 12 against the body member 11. The $F_X$ force component varies the tension in the cuff 33, whereas the $F_Y$ force component varies the tension in the stirrup region of the body member. In combination, the $F_R$ resultant force component permits simultaneous tensioning in the cuff and stirrup region of the body member 11.

In detail, $F_X$ force component results in cylindrical tightening of the cuff 33 which promotes the reduction of the high-ankle sprain injury (i.e., syndesmosis). The cuff 33 of the body member 11 is therefore dynamic in the sense that the cuff member 13 promotes increased compression when the stabilizing strap 12 is tightened during application (i.e., securing the apparatus 10 to the foot) and use (i.e. when the apparatus actively restricts ankle rotation). Advantageously, the dynamic tightening of the cuff 33 minimizes the effects of syndesmosis in a novel manner by applying increased compression in the cuff 33 the moment the foot is under load and rotates excessively (e.g., changing directions when running).

In further detail, the $F_Y$ force component varies the tension in the interior stirrup region of the body member 11. When placing the apparatus 10 on the foot, the user may adjust tension applied by portions of the stabilizing strap 12 positioned against interior surfaces of the body member 11 (i.e., stirrup region) by pulling on the stabilizing strap after securely lacing the boot.

Advantageously, the resultant force ($F_R$) provides the simultaneous tensioning of portions of the strap 12 positioned against the interior and exterior surfaces 31, 32 of the body member 11. Stated differently, the novel configuration of the cuff member 13 and stabilizing strap 12 simultaneously permits the tensioning of strap portions positioned against the interior and exterior surfaces 31, 32 of the body member 11.

As applied to the foot and ankle, the cuff member 13 directs a first force (i.e., vertical compression) against sections of the ankle proximate a portion of the stabilizing strap 12 that is interior of the flexible body member 11. The cuff member 13 further directs a second force (i.e., circumferential compression) against sections of the ankle proximate a portion of the stabilizing strap that is exterior of the flexible body member 11 in addition to the first force. Stated differently, the cuff member 13 directs a first and second force applied by the stabilizing strap 12 against the flexible body member and ankle.

For example, the stabilizing strap 12 and cuff member 13 engage one another to dynamically vary the circumference of the upper portion 25 of the flexible body member 11 during application and use. It will be understood that variations in the circumference of the upper portion 25 of the body member does not mean the material forming the body member expands, stretches, or elongates. Rather, variations in the circumference of the upper portion 25 refer to the bunching and expanding of the upper portion resulting from the compressive forces applied by the stabilizing strap against the cuff.

Further, the stabilizing strap 12 and cuff member 13 engage one another to dynamically vary the vertical compression acting on the flexible body member 11 during application and use. Still further, the stabilizing strap 12 and cuff member 13 engage one another to dynamically vary the circumferential compression acting on the body member during application and use.

In one embodiment shown in FIG. 8, the opening 45 in the cuff member 13 is an elongate slot that extends substantially adjacent to and along a lower edge 48 of the cuff member in non-parallel fashion with respect to an upper edge 47 of the cuff member. Stated differently, the elongate slot 45 is positioned oblique to one edge of the cuff member 13. The opening 45 redirects the force applied by the stabilizing strap 12 against the flexible body member 11. In another embodiment (not shown), the cuff member 13 may include one or more cut-outs along one or more edges such that the cut-outs engage or slidably receive portions of the stabilizing strap 12 and direct the forces applied by the strap against the body member 11.

As illustrated, the cuff member 13 is substantially triangular. Nevertheless, the cuff member 13 may also be substantially rectangular, substantially polygonal, or substantially circular, or any number of shapes sufficient to engage the stabilizing strap 12 and provide a fixed point from which the stabilizing strap extends from the body member 11. It will be understood that the terms "substantially triangular", "substantially rectangular", "substantially polygonal" and "substantially circular" are meant to succinctly describe a simple geometric shape approximating a triangle, rectangle, polygon, or circle, respectively.

The cuff member 13 may also include a cut-out 49 at a lower edge 48. The cut-out minimizes contact with (and hence irritation of) the upper portion of the Achilles tendon (i.e., calcaneal tendon) during activity. The cuff member may also provide one or more openings 46 for securing portions of the cuff member to the body member (e.g., with an eyelet fastener and lace). The cuff member 13 may be formed from any number of inelastic materials (e.g. polymeric material) that provide a semi-rigid characteristic to the cuff member.

The flexible body member 11 may further define at least one opening 35 that corresponds to the opening 45 in the cuff member 13. As illustrated in FIGS. 2 and 5, the body member opening 35 and the cuff member opening 45 direct the stabilizing strap 12 from a position interior of the flexible body member to a position exterior of the body member. Advantageously, the openings 35, 45 direct the stabilizing strap 12 from a fixed point on the first or second sides 29, 30 of the body member 11.

Stated differently, the cuff member 13 provides a fixed point on the upper portion 25 of the flexible body member 11 from which the stabilizing strap 12 extends such that the cuff member 13 and stabilizing strap increase compression at the cuff 33 and resist distal migration of the apparatus 10 upon increased tension applied to the stabilizing strap during application and use. In novel fashion, the cuff member 13 provides a fixed point on the upper portion 25 of the first and second sides 29, 30 of the body member 11. Advantageously, the fixed point provides an elevated anchor point from which the cuff member 13 and stabilizing strap 12 provide variable compression against the body member and ankle in dynamic fashion to prevent sprains and resist distal migration.

As depicted in FIGS. 6 and 7, the invention also provides padding 21 secured to the interior surface 31 of the body member 11 and positioned substantially adjacent to the cuff member 13. The padding 21 may be a sheet or sheets of foam material. It will be understood that the padding 21 may be continuous or patterned.

The cuff enclosure 14 positions the cuff member 13 against the cuff 33 of the body member 11. In other words, the cuff enclosure 14 positions the cuff member 13 against the upper and/or rear portions 25, 28 of the body member 11. As set forth above, distal migration affects flexible ankle apparatus 10 and results in loosening of the stabilizing strap 12 during and after application. Any upward force exerted by the stabilizing strap 12 on the foot and ankle in the process of counteracting rotation is met with an equal and opposite downward force on the upper portion 25 of the apparatus 10 where the stabilizing strap 12 is removably attached (i.e., adjustably secured) to the exterior surface 32 of the body member 11. The downward force contributes to distal migration of the body member 11 by drawing the upper portion 25 of the body member downward and towards the distal end of the leg.

The dynamic cuff and stabilizing strap system of the present invention resists distal migration of the apparatus 10 with a body member 11 having an inverted, truncated cone shape which mirrors the anatomy of the lower leg, in addition to the aforementioned variable compression which increases with increased foot rotation. The inverted, truncated cone shape of the cuff 33 is achieved by introducing variable thickness in the vertical direction of the cuff enclosure 14 as illustrated in FIG. 9. As used herein, the term "thickness" refers to the shortest dimension between two surfaces of an object (e.g., cuff enclosure 14) as opposed to the width or the length.

Variable thickness in the cuff 33 is accomplished by incorporating a flexible sheet member 52 such as a strip of fabric on the interior surface of the cuff enclosure 14. Stated differently, the flexible sheet member is positioned on the surface of the cuff enclosure 14 substantially adjacent to the interior surface 31 of the body member 11. As illustrated in the embodiment of FIG. 8, the flexible sheet member 52 partially encircles the inferior or lower portion of the cuff enclosure 14. The application of the flexible sheet member 52 results in an increased circumference of the lower cuff 33 near the minimum width of the leg just above the malleolli of the ankle. Thus, the flexible sheet member compensates for the decreasing thickness of the leg from the proximal to distal end. In one embodiment, the thickness of the cuff 33 is approximately 33% greater near the lower edge of the cuff member 13 where the ankle is narrower. This configuration permits an outermost binding strap 15, which may cover the cuff 33 as the final step in application, to compress the cuff in a more uniform fashion because the exterior surface 32 of the cuff 33 of the body member 11 defines a more geometrically accurate cylindrical shape.

In one embodiment depicted in FIG. 8, the flexible sheet member 52 extends along at least a portion of a lower edge of the cuff enclosure. As illustrated in FIG. 9, the thickness of an upper portion of the cuff enclosure 14 is less than the thickness of a lower portion of the cuff enclosure. As discussed above, flexible sheet member 52 increases the circumference of the lower cuff of the body member 11 adjacent to the minimum thickness of the leg just above the malleolli of the ankle. Thus, the interior surface 31 of the body member 11 that is applied against the lower leg substantially define an inverted, truncated cone that conforms to the contour of the ankle and lower leg, and the exterior surface 32 of the body member is substantially cylindrical. In other words, the flexible sheet member 52 and cuff enclosure 14 compensate for the reduced thickness of the lower leg above the ankle, and provides a cylindrical outer surface against which the binding strap 15 may be applied to more uniformly compress the lower leg and minimize eversion and inversion. Accordingly, the cuff enclosure 14 and the cuff member 13 resist distal migration of the upper portion 25 of the flexible body member 11 by distributing the compression forces acting against the flexible body member.

In one embodiment, the cuff enclosure 14 is fixed or releasably attached to the interior surface 31 of the body member 11. In this embodiment, the cuff member 13 is positioned against the interior surface of the body member 11.

In an alternative embodiment (not shown), the cuff enclosure 14 is fixed or releasably attached to the exterior surface 32 of the body member 11. In this alternative embodiment, the cuff member 13 is positioned against the exterior surface 32 of the body member 11. This alternative embodiment (not shown) further includes at least one stabilizing strap 12 having a fixed end and a free end, wherein the fixed end is secured to the exterior surface 32 of the lower portion 26 of the body member 11. The stabilizing strap 12 extends upward from the lower portion 26 of the body member 11, along the exterior surface 32 of the body member 11, and between the exterior surface of the body member and an interior surface of the cuff enclosure 14. Thereafter, the stabilizing strap 12 moves into an opening 45 in the cuff member 13 and the cuff enclosure 14, and outwardly exterior of the cuff enclosure.

The cuff enclosure 14 secures selected portions of the cuff member 13 to the body member 11. In certain embodiments, the cuff enclosure 14 also provides a layer between the cuff member 13 and the user's leg. It will also be understood that as used herein, the concept of an element (e.g., padding) being "between" two other elements does not necessarily imply that the three elements are contiguous (i.e., in intimate contact). Rather, as used herein, the concept of one element being between two other elements is meant to describe the relative positions of the elements within the apparatus 10 structure, respectively.

As seen in FIG. 6, the cuff enclosure 14 is secured to the interior surface 31 of the upper portion 25 of the body member 11. In one embodiment, the cuff enclosure 14 is secured to interior surfaces 31 of the upper portion 25, first side 29, and second side 30 of the body member 11. It will be understood, however, that the cuff enclosure 14 may be secured only to one of the sides 29, 30, or only to the upper portion 25, or only to the rear portion 28. The cuff enclosure 14 may also be secured to any combination of the upper portion 25, rear portion 28, and sides 29, 30. Still referring to FIG. 8, the cuff enclosure 14 may extend substantially coextensive with the upper portion 25 and first and second sides 29, 30 of the body member 11 (i.e., substantially coextensive with the cuff 33).

The binding strap 15 is positioned against the upper portion 25 of the flexible body member 11 and includes at least one free end that is releasably attachable to the flexible body member. The binding strap 15 is configured to loop about the upper ankle of the wearer so as to overlie portions of the stabilizing strap 12, lace 18, and eyelets 17 of the apparatus 10. In one embodiment, the binding strap 15 is secured to the rear portion 28 of the body member 11, and includes two free ends as illustrated in FIGS. 1, 2, and 7. In this fashion, the binding strap 15 may be wrapped circumferentially about the individual's ankle to secure the body member 11 and cuff member 13 more securely to the individual's foot. Though specifically illustrated in FIG. 2 as being in the form of a single binding strap 15 secured to the rear portion 28 of the body member 11 to thereby provide two free ends, it will be appreciated that a single strap could be secured at one end and have a single free end which wraps around the individual's ankle. Alternatively, a plurality of straps may form the binding strap 15.

The binding strap 15 desirably extends laterally from the rear portion 28 of the body member 11 to overlie at least a portion of the stabilizing strap 12. The free ends of the binding strap 15 are secured so that the binding straps encircle the individual's ankle by way of a pair of corresponding fasteners 55*a*, 55*b*. The pair of corresponding fasteners 55*a*, 55*b* may be secured to free ends of the binding strap 15 such that the free ends engage one another when wrapped around the ankle and extended against one another in overlying fashion. The fasteners 55*a*, 55*b* are desirably of the hook and loop fastener variety, though other types of fasteners may be used. In one embodiment of the invention, the binding strap 15 is made from an elastic fabric material. As configured, the binding strap 15 applies yet another force (i.e., third force) against the flexible body member 11, portions of the cuff enclosure 14 and cuff member 13, and the ankle and foot.

With reference to FIGS. 1, 2, and 3, the ankle stabilizing apparatus 10 further provides a body member connector 16 for securing free front edges of body member 11 to one another. The body member connector 16 facilitates the drawing of the front edges of the body member 11 towards one another to secure the apparatus 10 about the ankle and foot. In one embodiment, the body member connector 16 may comprise a plurality of eyelets 17 defined by and extending along front edges of the body member 11, a plurality of eyelets 17 defined by and extending along edges of the cuff enclosure 14, and at least one lace 18 threaded through the respective eyelets. At least one of the eyelets 17 of the body member connector 16 corresponds with one of the openings 46 of the cuff member 13. It will be understood, however, that the body member connector 16 may include any number of devices capable of drawing the front edges of the body member 11 together.

As depicted in FIGS. 1, 2, and 3, a tongue 60 is secured between the opposing free front edges of the body member 11. The tongue 60 may be composed of a padded fabric. The tongue 60 assists to secure the body member 11 to the foot of the individual, and provides padding 21 between the body member connector 16 and the individual's foot.

In an alternative embodiment (not shown), the apparatus 10 may include two stabilizing straps 12, a first and a second, for each side 29, 30 of the body member 11. Stated differently, the apparatus may provide four stabilizing straps. In this alternative embodiment the apparatus 10 includes the flexible body member 11 as described above in various embodiments, a first stabilizing strap 12 for applying one force against the flexible body member, a second stabilizing strap 12 for applying another force against the flexible body member, and a cuff member 13 for directing the forces applied by the stabilizing straps against the flexible body member.

The first stabilizing strap 12 has one portion positioned against (i.e., fixed or releasably attached to) the lower portion 26 of the flexible body member 11, and another portion positioned against the upper portion 25 of the body member. Specifically, the first stabilizing strap 12 has a fixed end secured to the interior surface 31 of the lower portion 26 of the body member 11. A free end of the first strap is releasably attached to the exterior surface 32 of the upper portion 25 of the body member at one of the first or second sides 29, 30. The first stabilizing strap 12 extends upwardly from the lower portion 26 of the body member 11, along the interior surface 31, through the corresponding openings 45, 35 of the cuff member 13 and body member 11, and exterior of the body member to releasably attach to the one side of the body member.

The second stabilizing strap 12 has one portion positioned against (i.e., fixed or releasably attached to) the upper portion 25 of the body member 11, and another portion positioned against the upper portion 25 of body member substantially adjacent to the free end of the first stabilizing strap 12. More specifically, the second stabilizing strap 12 has a fixed end secured to the exterior surface 32 of the upper portion 25 of the body member 11 substantially adjacent to the corresponding openings 45, 35 in the cuff member 13 and body member 11. A free end of the second strap is releasably attached to the exterior surface 32 of one of the first or second sides 29, 30 of the upper portion 25 of the body member 11. The free end of the second strap is releasably attached substantially adjacent to the free end of the first stabilizing strap 12.

The second stabilizing strap 12 extends from the upper portion 25 of the body member 11, across the front portion 27 of body member, under the lower portion 26 of the body member, and upwardly along the exterior surface 32 of one side of the flexible body member in a FIG. 8 fashion. As set forth above, the free end of the second stabilizing strap is releasably attached to the exterior surface 32 of the upper portion 25 of the body member 11 substantially adjacent to or against the free end of the first stabilizing strap 12. As positioned, the free end of the second stabilizing strap 12 overlies at least portion of the free end of the first stabilizing strap to sandwich the free end of the first strap between the body member 11 and the second strap. A pair of corresponding fasteners is provided on the exterior surfaces of the upper portion of the body member and free ends of the first and second straps to releasably attach the ends thereto. The free end of the first stabilizing strap may include fasteners on both sides such that the free end of the second stabilizing strap is releasably attached to the surface of the free end of the first strap.

In this alternative embodiment, the cuff member 13 as described above in various embodiments is positioned against the interior or exterior surface 32 of the rear portion 28 of the flexible body member 11.

In another alternative embodiment (not shown), the apparatus may include three stabilizing straps, wherein the first stabilizing strap 12 has an intermediate portion positioned against (i.e., fixed or releasably attached to) the interior surface 31 of the lower portion 26 of the body member 11. Free ends of the first strap are releasably attached to the exterior surface 32 of the upper portion 25 of the body member at each of the first and second sides 29, 30. The first stabilizing strap 12 extends upwardly from the lower portion 26 of the body member 11 along the interior surface 31 of both sides 29, 30 of the body member, through each of the corresponding openings 45, 35 of the cuff member 13 and body member 11, and exterior of the body member to releasably attach to both sides 29, 30 of the body member.

Each of the second and third stabilizing straps have one end positioned against (i.e., fixed or releasably attached to) the exterior surface 32 of the upper portion 25 of the body member 11 substantially adjacent to each of the corresponding openings 45, 35 in the cuff member 13 and body member 11. Free ends of each of the second and third straps are releasably attached to the exterior surface 32 of both sides 29, 30 of the upper portion 25 of the body member 11. The free ends of the second and third straps are releasably attached substantially adjacent to the free ends of the first stabilizing strap 12.

In this alternative embodiment, the second and third stabilizing straps 12 extend from the upper portion 25 of the body member 11, across the front portion 27 of body member, under the lower portion 26 of the body member, and upwardly along the exterior surface 32 of each side 29, 30 of the body member in a FIG. 8 or overlying fashion. As set forth above, the free ends of the second and third stabilizing straps are releasably attached to the exterior surface 32 of the upper portion 25 of the body member 11 substantially adjacent to or against the free ends of the first stabilizing strap. As positioned, the free ends of the second and third stabilizing straps 12 overlie at least portion of the free ends of the first stabilizing strap to sandwich the free ends of the first strap between the body member 11 and the second and third straps. Pairs of corresponding fasteners are provided on the exterior surface 32 of the upper portion 25 of the body member 11, and free ends of the first, second, and third straps to releasably attach the ends thereto. The free ends of the first stabilizing strap may include fasteners on both sides such that the free ends of the second and third stabilizing straps are releasably attached to the surface of the free end of the first strap.

In operation, the body member 11 is first placed on the individual's foot. Once the body member 11 is secured to the foot, the lace 18 is drawn tight and secured (e.g., by tying the lace into a knot). In an exemplary description, one stabilizing strap is brought across the first side 29 of the body member 11, over the front portion 27 of the body member and top of the individual's foot, downwardly across the inside of the foot, and across the stirrup portion of the body member 11 under the foot. The stabilizing strap is then brought upwardly so that the fastener 40b on the free end thereof can be attached to its corresponding fastener 40a located on the exterior surface 32 of the first side 29 of the body member 11.

The other stabilizing strap is then wrapped around the individual's foot by bringing it across the second side 30 of the body member 11, over the front portion 27 of the body member and top of the individual's foot, downwardly across the outside of the foot, and across the stirrup portion of the body member 11 under the foot. The stabilizing strap is then brought upwardly so that the fastener 40b on the free end thereof can be secured to the fastener 40a located on the exterior surface 32 of the second side 30 of the body member 11. Thereafter the binding strap 15 is secured around the upper portion 25 of the body member and ankle for secure fitment.

In the drawings and specification, there have been disclosed typical embodiments of the invention and, although specific terms have been employed, they have been used in a generic and descriptive sense only and not for purposes of limitation, the scope of the invention being set forth in the following claims.

That which is claimed is:

1. An ankle stabilizing apparatus for stabilizing movement of an ankle, said ankle stabilizing apparatus comprising:
   a flexible body member having an upper portion, a lower portion, an interior surface, and an exterior surface;
   at least one stabilizing strap for applying at least one force against said flexible body member, said at least one stabilizing strap having at least one portion positioned against said flexible body member; and
   a cuff member for directing the at least one force applied by said at least one stabilizing strap against said flexible body member, said cuff member positioned against said flexible body member, said cuff member defining at least one opening for receiving and redirecting a portion of said at least one stabilizing strap.

2. The ankle stabilizing apparatus according to claim 1, wherein said at least one stabilizing strap and said cuff member engage one another to dynamically vary the circumference of said upper portion of said flexible body member during application and use.

3. The ankle stabilizing apparatus according to claim 1, wherein said at least one stabilizing strap and said cuff member engage one another to dynamically vary the vertical compression acting on said flexible body member during application and use.

4. The ankle stabilizing apparatus according to claim 1, wherein said at least one stabilizing strap and said cuff member engage one another to dynamically vary the circumferential compression acting on said flexible body member during application and use.

5. The ankle stabilizing apparatus according to claim 1, wherein said flexible body member defines at least one opening for directing said at least one stabilizing strap from a position interior of said flexible body member to a position exterior of said flexible body member.

6. The ankle stabilizing apparatus according to claim 1, wherein:
   said at least one stabilizing strap has at least another portion removably attachable to said exterior surface of said upper portion of said flexible body member; and
   said at least one portion of said at least one stabilizing strap is fixed against said interior surface of said lower portion of said flexible body member.

7. The ankle stabilizing apparatus according to claim 1, wherein a portion of said at least one stabilizing strap extends substantially along a portion of said interior and exterior surfaces of said flexible body member.

8. The ankle stabilizing apparatus according to claim 1, wherein said cuff member is positioned against said interior surface of said flexible body member.

9. The ankle stabilizing apparatus according to claim 1, wherein said cuff member is positioned against said exterior surface of said flexible body member.

10. The ankle stabilizing apparatus according to claim 1, wherein said cuff member directs said at least one stabilizing strap from a position interior of said flexible body member to a position exterior of said flexible body member.

11. The ankle stabilizing apparatus according to claim 1, wherein said cuff member provides a fixed point on said upper portion of said flexible body member from which said at least one stabilizing strap extends such that said cuff member and said at least one stabilizing strap resist distal migration of said apparatus during application and use.

12. The ankle stabilizing apparatus according to claim 1, comprising a cuff enclosure for positioning said cuff member against said flexible body member.

13. The ankle stabilizing apparatus according to claim 1, wherein said at least one opening defined by said cuff member comprises an angled, elongate slot configured to receive and redirect a portion of said at least one stabilizing strap.

14. An apparatus for stabilizing movement of an ankle, said ankle stabilizing apparatus comprising:
    a flexible body member for receiving a foot and ankle, said flexible body member having an upper portion, a lower portion, an interior surface, and an exterior surface, said flexible body member defining at least one opening for receiving at least a portion of a heel;
    at least one stabilizing strap for securing said flexible body member to a foot and ankle, said at least one stabilizing strap having at least one portion positioned against said flexible body member and having at least one free end removably attachable to said exterior surface of said flexible body member; and
    a cuff member for redirecting at least one force applied by said at least one stabilizing strap against said flexible body member and ankle, said cuff member positioned against said upper portion of said flexible body member, said cuff member defining at least one opening for receiving and redirecting a portion of said at least one stabilizing strap.

15. The ankle stabilizing apparatus according to claim 14, wherein said cuff member directs a first force against sections of the ankle proximate a portion of said at least one stabilizing strap that is interior of said flexible body member.

16. The ankle stabilizing apparatus according to claim 15, wherein said cuff member directs a second force against sections of the ankle proximate a portion of said at least one stabilizing strap that is exterior of said flexible body member in addition to the first force.

17. The ankle stabilizing apparatus according to claim 14, wherein said at least one cuff member opening is positioned oblique to at least one edge of said cuff member, said at least one cuff member opening for redirecting the at least one force applied by said at least one stabilizing strap against said flexible body member and ankle.

18. The ankle stabilizing apparatus according to claim 14, comprising a cuff enclosure for positioning said cuff member against said flexible body member.

19. The ankle stabilizing apparatus according to claim 18, wherein said cuff enclosure and said cuff member resist distal migration of said upper portion of said flexible body member by distributing the at least one force acting against said flexible body member.

20. The ankle stabilizing apparatus according to claim 18, wherein the thickness of an upper portion of said cuff enclosure is less than the thickness of a lower portion of said cuff enclosure.

21. The ankle stabilizing apparatus according to claim 18, wherein said cuff enclosure comprises a flexible sheet member extending along at least a portion of a lower portion of said cuff enclosure.

22. The ankle stabilizing apparatus according to claim 14, wherein said at least one cuff member opening comprises an angled, elongate slot configured to receive and redirect a portion of said at least one stabilizing strap.

23. An ankle stabilizing apparatus, comprising:
    a flexible body member for receiving a foot and ankle;
    a first stabilizing strap having at least one portion positioned against said flexible body member and having at least another portion removably attachable to said flexible body member;
    a second stabilizing strap having at least one portion positioned against said flexible body member and having at least another portion removably attachable to said flexible body member; and
    a cuff member defining at least one angled, elongate opening for receiving and redirecting a portion of at least one of said first and second stabilizing straps, said cuff member affixed to said flexible body member.

24. The ankle stabilizing apparatus according to claim 23, wherein at least one of said stabilizing straps and said cuff member engage one another to dynamically vary compression acting on said flexible body member during application and use to stabilize movement of the foot and ankle.

25. The ankle stabilizing apparatus according to claim 23, wherein said stabilizing straps and said cuff member engage one another to dynamically vary the vertical compression and circumferential compression acting on said flexible body member during application and use.

26. The ankle stabilizing apparatus according to claim 23, wherein said cuff member defines (i) a first angled, elongate opening that receives and redirects a portion of said first stabilizing strap and (ii) a second angled, elongate opening that receives and redirects a portion of said second stabilizing strap.

27. An apparatus for stabilizing ankle movement, comprising:
    a flexible body member for receiving a foot and ankle, said flexible body member having an upper portion, a lower portion, an interior surface, and an exterior surface;
    a stabilizing strap having (i) an inner stirrup portion positioned substantially adjacent to said interior surface of said flexible body member and (ii) an outer stabilizing portion positioned substantially adjacent to said exterior surface of said flexible body member; and
    a cuff member positioned against said upper portion of said flexible body member, said cuff member defining an elongate slot for receiving said stabilizing strap, wherein said elongate slot of said cuff member is obliquely angled with respect to said inner stirrup portion of said stabilizing strap.

28. The apparatus for stabilizing ankle movement according to claim 27, wherein a portion of said inner stirrup portion of said stabilizing strap is affixed to said interior surface of said flexible body member.

29. The apparatus for stabilizing ankle movement according to claim 27, wherein a portion of said outer stabilizing portion of said stabilizing strap is removably attachable to said exterior surface of said flexible body member.

30. The apparatus for stabilizing ankle movement according to claim 27, wherein said cuff member is affixed to said upper portion of said flexible body member.

31. An apparatus for stabilizing ankle movement, comprising:

a flexible body member for receiving a foot and ankle, said flexible body member having an upper portion, a lower portion, an interior surface, and an exterior surface;

a cuff member positioned against said upper portion of said flexible body member, said cuff member defining an elongate slot; and a stabilizing strap passing through said elongate slot of said cuff member, said stabilizing strap having (i) an inner stirrup portion positioned substantially adjacent to said interior surface of said flexible body member and (ii) an outer stabilizing portion positioned substantially adjacent to said exterior surface of said flexible body member;

wherein, as said stabilizing strap passes through said elongate slot of said cuff member, said elongate slot of said cuff member is obliquely angled with respect to said inner stirrup portion of said stabilizing strap.

32. The apparatus for stabilizing ankle movement according to claim 31, wherein a portion of said inner stirrup portion of said stabilizing strap is affixed to said interior surface of said flexible body member.

33. The apparatus for stabilizing ankle movement according to claim 31, wherein a portion of said outer stabilizing portion of said stabilizing strap is removably attachable to said exterior surface of said flexible body member.

34. The apparatus for stabilizing ankle movement according to claim 31, wherein said cuff member is affixed to said upper portion of said flexible body member.

35. An apparatus for stabilizing ankle movement, comprising:

a flexible body member for receiving a foot and ankle, said flexible body member having an upper portion, a lower portion, an interior surface, and an exterior surface;

a stabilizing strap having (i) an inner stirrup portion positioned substantially adjacent to said interior surface of said flexible body member and (ii) an outer stabilizing portion positioned substantially adjacent to said exterior surface of said flexible body member; and a strap-redirecting member positioned against said upper portion of said flexible body member, said strap-redirecting member defining at least one opening for receiving and redirecting said stabilizing strap.

36. The apparatus for stabilizing ankle movement according to claim 35, wherein said strap-redirecting member's at least one opening for receiving and redirecting said stabilizing strap comprises an elongate slot obliquely angled with respect to said inner stirrup portion of said stabilizing strap.

* * * * *

UNITED STATES PATENT AND TRADEMARK OFFICE
CERTIFICATE OF CORRECTION

PATENT NO. : 9,737,430 B2  
APPLICATION NO. : 14/275092  
DATED : August 22, 2017  
INVENTOR(S) : Eric Lee Gaylord Page 1 of 1

It is certified that error appears in the above-identified patent and that said Letters Patent is hereby corrected as shown below:

In the Claims

Claim 1, Column 16, delete Lines 13-15 and insert: --An apparatus for stabilizing movement of an ankle, the ankle stabilizing apparatus comprising:--

Claim 14, Column 17, delete Line 18 and insert: --the ankle stabilizing apparatus comprising:--

Signed and Sealed this  
Fifth Day of June, 2018

Andrei Iancu  
*Director of the United States Patent and Trademark Office*